United States Patent [19]
Winterborn

[11] Patent Number: 6,063,802
[45] Date of Patent: May 16, 2000

[54] ONDANSETRON FREEZE-DRIED DOSAGE FORM COMPOSITIONS FOR ORAL ADMINISTRATION

[75] Inventor: Ian Keith Winterborn, Ware, United Kingdom

[73] Assignee: Glaxco Wellcome Inc., Mississauga, Canada

[21] Appl. No.: 09/238,165

[22] Filed: Jan. 28, 1999

Related U.S. Application Data

[63] Continuation of application No. 09/066,762, Apr. 28, 1998, Pat. No. 5,955,488, which is a continuation of application No. 08/906,839, Aug. 6, 1997, abandoned, which is a continuation of application No. 08/557,620, Nov. 14, 1995, abandoned.

[30] Foreign Application Priority Data

Nov. 22, 1994 [GB] United Kingdom .................. 9423511

[51] Int. Cl.⁷ .................................................. A61K 31/415
[52] U.S. Cl. ............................................................. 514/397
[58] Field of Search ............................................. 514/397

[56] References Cited

U.S. PATENT DOCUMENTS

| | | | |
|---|---|---|---|
| 4,754,597 | 7/1988 | Buxton et al. | 53/440 |
| 4,929,632 | 5/1990 | Tyers et al. | 514/397 |
| 5,046,618 | 9/1991 | Wood | 206/532 |
| 5,188,825 | 2/1993 | Iles et al. | 424/78.1 |
| 5,288,497 | 2/1994 | Stanley et al. | 424/440 |
| 5,785,989 | 7/1998 | Stanley et al. | 424/440 |

OTHER PUBLICATIONS

Remington's Pharmaceutical Sciences, 16th ed. pp 1111 and 1225–1227, 1980.

*Primary Examiner*—Raymond Henley, III
*Attorney, Agent, or Firm*—Bacon & Thomas

[57] ABSTRACT

The invention relates to a freeze-dried dosage form for oral administration capable of being rapidly disintegrated in the mouth comprising ondansetron in the form of its free base or a pharmaceutically acceptable solvate thereof and one or more pharmaceutically acceptable excipients. Methods for the manufacture of such compositions and for their use in the treatment of conditions mediated through the action of 5-hydroxytryptamine (5HT) at $5HT_3$ receptors are also described.

10 Claims, No Drawings

ONDANSETRON FREEZE-DRIED DOSAGE FORM COMPOSITIONS FOR ORAL ADMINISTRATION

This application is a continuation of application Ser. No. 09/066,762, filed Apr. 28, 1998, now U.S. Pat. No. 5,955,488 which is a continuation of application Ser. No. 08/906,839, filed Aug. 6, 1997 abandoned, which is a Rule 1.62 file wrapper continuation of application Ser. No. 08/557,620, filed Nov. 14, 1995, which is abandoned.

The present invention relates to a pharmaceutical composition containing, as active ingredient, 1,2,3,9-tetrahydro-9-methyl-3-[(2-methyl-1H-imidazol-1-yl)methyl]-4H-carbazol-4-one, in particular a freeze-dried dosage form that disintegrates rapidly, for oral administration.

In UK Patent No. 2153821B we disclose, inter alia, 1, 2, 3, 9-tetrahydro-9-methyl-3-[(2-methyl-1H-imidazol-1-yl)methyl]-4H-carbazol-4-one, now known as ondansetron, which may be represented by the formula (I)

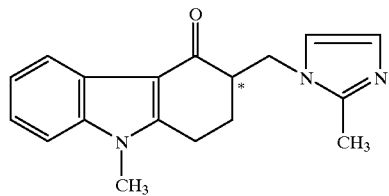

and physiologically acceptable salts, solvates and physiologically acceptable equivalents thereof.

Ondansetron is a highly selective and potent antagonist of 5-hydroxytryptamine (5HT) at $5HT_3$ receptors and may be used in the treatment of a variety of conditions ameliorated by administration of $5HT_3$ receptor antagonists, such as emesis (as described in European Patent Application Publication Nos. 226266 and 201165) and anxiety.

Numerous clinical studies have demonstrated the effectiveness of ondansetron for the treatment of emesis, particularly the nausea and vomiting associated with cancer chemotherapy and radiotherapy and that occurring post-operatively. Hitherto, ondansetron has always been administered in the form of a salt, in particular in the form of its hydrochloride dihydrate, either by injection or orally.

Oral administration in the form of a conventional tablet, pill or capsule constitutes the generally preferred route for administration of pharmaceuticals since this route is generally convenient and acceptable to patients. Unfortunately such compositions may be associated with certain disadvantages, particularly in the treatment of paediatric or geriatric patients, who may dislike or have difficulty in swallowing such compositions, or where administration of a conventional tablet, pill or capsule is not feasible. It is highly desirable, particularly in the treatment of acute conditions, that pharmaceutical compositions have a rapid and consistent onset of action combined with sustained activity and good bioavailability. Rapid absorption can be achieved by parenteral injection but this is unacceptable to some patients, particularly if the drug is to be administered without direct medical supervision, i.e. self-administered.

One way to overcome this problem is to administer a solid dosage form that disintegrates rapidly in the mouth, such as a freeze-dried solid dosage form, for example as described in UK Patent Nos. 1548022, 2111423, 2119246, 2114440, 2111184, 2120370, and U.S. Pat. Nos. 5,046,618 and 5,188,825, all incorporated herein by reference.

We have found that ondansetron hydrochloride dihydrate, in common with many drug substances has, however, an inherently bitter taste, and this constitutes a disadvantage for a solid dosage form that disintegrates rapidly in the mouth. Moreover, it is well known that patients may not complete a necessary course of medicine if they are prescribed an oral presentation which is particularly unpleasant to taste. To some extent the bitter taste may be masked by the use of sweetening and/or flavouring aids, although this is not entirely satisfactory, and an unpleasant after-taste may still remain in the mouth. In addition, there may be circumstances in which it is undesirable or inappropriate to use a sweetening and/or flavouring aid.

We have now found, surprisingly, that a freeze-dried dosage form that disintegrates rapidly in the mouth, comprising ondansetron in the form of its free base, provides a particularly advantageous pharmaceutical composition.

The present invention therefore provides in a first aspect a freeze-dried dosage form for oral administration capable of being rapidly disintegrated comprising ondansetron in the form of its free base or a pharmaceutically acceptable solvate thereof and one or more pharmaceutically acceptable excipients.

By "rapidly disintegrated" is meant that the dosage forms are disintegrated in water within ten seconds when tested by the procedure disclosed in UK Patent No. 1548022. Preferably the dosage forms disintegrate within 5 seconds, or less.

Preferably the freeze-dried dosage forms according to the invention comprise ondansetron in the form of its free base.

It will be appreciated by those skilled in the art that ondansetron contains one chiral centre (shown by * in the formula (I)) and that ondansetron therefore exists in the form of optical isomers (i.e. enantiomers). The invention includes all isomers of ondansetron and its pharmaceutically acceptable solvates, including all tautomeric and optical forms, and mixtures thereof, including racemic mixtures.

Conveniently ondansetron, expressed as free base, may comprise 0.1 to 10% weight by weight (w/w) of the composition, such as 1 to 5% w/w, preferably 2.5 to 4% w/w, for example about 3.2% w/w.

The amount of ondansetron in the freeze-dried dosage form, expressed as free base, is conveniently in the range 0.1 to 100 mg, such as 0.5 to 50 mg, preferably 1 to 25 mg, such as 4 or 8 mg.

The freeze-dried dosage forms of the invention are, surprisingly, free of the bitter taste associated with corresponding compositions comprising ondansetron hydrochloride dihydrate.

To be capable of being disintegrated rapidly, the freeze-dried dosage form may comprise a network of pharmaceutically acceptable water soluble or water-dispersible carrier material, conveniently as described in the patents incorporated herein by reference above, for example, in UK Patent No 1548022. Suitable materials to act as a carrier material include, for example, gelatin (including partially hydrolysed gelatin), polysaccharides such as hydrolysed dextran, dextrin and alginates (e.g. sodium alginate) or mixtures of the above mentioned carriers with each other with other carrier materials such as polyvinyl alcohol, polyvinylpyrrolidine or acacia.

Conventional excipients which may also be employed in the freeze-dried dosage forms according to the invention include preservatives, flavouring aids, colouring aids, sweeteners, fillers, and mixtures thereof.

Suitable preservatives include one or more alkyl hydroxybenzoates or salts thereof, such as methyl, ethyl, propyl and/or butyl hydroxybenzoates; sorbic acid or a salt thereof;

benzoic acid or a salt thereof; and mixtures thereof. Preferably the freeze-dried dosage forms according to the invention comprise methyl- and propyl hydroxybenzoates, as their sodium salts.

Suitable flavouring aids include strawberry, cherry, mint and caramel flavouring aids, in particular strawberry flavouring aid.

Suitable sweeteners include, for example, sugars such as sucrose, lactose and glucose; cyclamate and salts thereof; saccharin and salts thereof; and aspartame. Preferably the sweetener of the freeze-dried dosage form of the invention is aspartame.

Suitable fillers include polyhydric alcohols, such as mannitol, sorbitol and xylitol, or mixtures thereof, which improve the physical properties of the freeze-dried dosage form. Preferably the freeze-dried dosage forms according to the invention comprise mannitol.

It will be appreciated by those skilled in the art that freeze-dried dosage forms capable of being disintegrated rapidly may be prepared by methods known in the art as, for example, described in the patents incorporated herein by reference above.

It will be further appreciated by those skilled in the art that the patents incorporated herein by reference above disclose suitable methods of packing the freeze-dried dosage forms of the invention.

Conveniently an aqueous composition of the components is prepared, poured into suitable moulds, frozen, and then sealed with a covering sheet adhered to the mould so as to enclose the dosage form. Preferably the dosage forms are packed in a double foil peel-back pack.

The weight of aqueous composition poured into a mould (the wet fill weight) is conveniently in the range 50 to 750 mg, such as 100 to 500 mg, for example 125 or 250 mg.

In a further preferred aspect, the invention provides a freeze-dried dosage form for oral administration capable of being disintegrated rapidly comprising ondansetron in the form of its free base, gelatin, sodium methylhydroxybenzoate, sodium propylhydroxybenzoate, strawberry flavouring aid, aspartame, and mannitol.

In a yet further preferred aspect, the invention provides a freeze-dried dosage form wherein the wet fill weight is 125 or 250 mg.

Within the above preferred aspects of the invention, a freeze-dried dosage form, wherein the amount of ondansetron is in the range 1 to 25 mg, such as 4 or 8 mg, is especially preferred.

In a further aspect the invention provides a method of treating a mammal, including man, suffering from a condition mediated through the action of 5HT at $5HT_3$ receptors, which comprises administration of a freeze-dried dosage form for oral administration capable of being rapidly disintegrated comprising ondansetron in the form of its free base or a pharmaceutically acceptable solvate thereof and one or more pharmaceutically acceptable excipients. It will be appreciated that reference to treatment is intended to include prophylaxis as well as the alleviation of established symptoms.

Conditions mediated through the action of 5HT at $5HT_3$ receptors include emesis; cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment; psychotic disorders, such as schizophrenia and mania; anxiety disorders, including panic disorder, agoraphobia, social phobia, simple phobia, obsessive compulsive disorders, post traumatic stress disorder, mixed anxiety and depression, and generalised anxiety disorder; irritable bowel syndrome and dependency on drugs and substances of abuse. Other conditions mediated in this manner include pruritis, particularly that induced by cholestasis; gastric stasis; symptoms of gastrointestinal dysfunction such as occur with peptic ulcer, reflux oesophagitis, flatulence and dyspepsia; migraine; obesity and conditions such as bulimia; pain; and depression.

Emesis, i.e. nausea, retching and vomiting, includes acute emesis, delayed emesis and anticipatory emesis. Ondansetron is useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; antimetabolites, e.g. cytarabine, methotrexate and 5- fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

The freeze-dried dosage forms according to the invention have particular utility for the treatment of emesis, particularly that associated with cancer chemotherapy and radiotherapy, but also that occurring post-operatively.

It will be appreciated that the precise therapeutic dose of the active ingredient will depend on the age and condition of the patient and the nature of the condition to be treated and will be at the ultimate discretion of the attendant physician.

However, in general, effective doses for the treatment of conditions mediated through the action of 5HT at $5HT_3$ receptors, for example emesis, will lie in the range of 0.05 to 100 mg, such as 0.1 to 50 mg, preferably 0.5 to 25 mg, for example 4, 8 or 16 mg of the active ingredient per unit dose, which could be administered in single or divided doses, for example, 1 to 4 times per day.

The following non-limiting examples further illustrate the invention.

EXAMPLE 1

|  | 125 mg | 250 mg | % w/w |
|---|---|---|---|
| Ondansetron Base | 4.0 | 8.0 | 3.2 |
| Gelatin Pharm Eur/USP | 5.0 | 10.0 | 4.00 |
| Mannitol Pharm Eur/USP | 3.75 | 7.5 | 3.00 |
| Aspartame USNF | 0.625 | 1.25 | 0.50 |
| Strawberry Flavouring Aid | 0.125 | 0.25 | 0.1 |
| Sodium Methylhydroxybenzoate | 0.0555 | 0.111 | 0.0444 |
| Sodium Propylhydroxybenzoate | 0.0070 | 0.014 | 0.0056 |
| Purified Water Pharm Eur/USP | qs to 125.0* | qs to 250.0* | qs to 100.0* |

*The water is removed during the freeze-drying process.

The components of the composition are mixed together as, for example, described in the patents incorporated herein by reference above.

The suspension is then poured into blister moulds. For 4 mg unit doses, the fill weight is 125 mg; for 8 mg unit doses the fill weight is 250 mg. The suspension is frozen, freeze-dried, and then sealed with a covering sheet adhered to the mould, as for example described in the patents incorporated herein by reference.

I claim:

1. A freeze-dried dosage form for oral administration capable of being rapidly disintegrated comprising ondansetron in the form of its free base or a pharmaceutically acceptable solvate thereof and one or more pharmaceutically acceptable excipients.

2. A composition according to claim 1 comprising ondansetron in the form of its free base.

3. A composition according to claim 1 wherein the amount of ondansetron, expressed as free base, is in the range 0.1 to 100 mg.

4. A composition according to claim 1 comprising ondansetron in the form of its free base, gelatin, sodium methylhydroxybenzoate, sodium propylhydroxybenzoate, strawberry flavouring aid, aspartame, and mannitol.

5. A composition according to claim 2 wherein the amount of ondansetron, expressed as free base, is in the range 0.1 to 100 mg.

6. A composition according to claim 2 comprising ondansetron in the form of its free base, gelatin, sodium methylhydroxybenzoate, sodium propylhydroxybenzoate, strawberry flavoring aid, aspartame, and mannitol.

7. A composition according to claim 3 comprising ondansetron in the form of its free base, gelatin, sodium methylhydroxybenzoate, sodium propylhydroxybenzoate, strawberry flavoring aid, aspartame, and mannitol.

8. A composition according to claim 4 which disintegrates rapidly in the mouth of a patient to which the composition has been administered.

9. A composition according to claim 1 which disintegrates in water within ten seconds.

10. A composition according to claim 9 which disintegrates in water within five seconds.

* * * * *